United States Patent
Redder et al.

(10) Patent No.: US 11,454,685 B2
(45) Date of Patent: Sep. 27, 2022

(54) MESH NETWORKS IN WIRELESS MRI RF COIL

(71) Applicant: KONINKLIJKE PHILIPS N.V., Eindhoven (NL)

(72) Inventors: Paul Franz Redder, Newberry, FL (US); Arne Reykowski, Newberry, FL (US); Rodrigo Calderon Rico, Newberry, FL (US)

(73) Assignee: Koninklijke Philips N.V., Eindhoven (NL)

( * ) Notice: Subject to any disclaimer, the term of this patent is extended or adjusted under 35 U.S.C. 154(b) by 63 days.

(21) Appl. No.: 16/766,050

(22) PCT Filed: Nov. 27, 2018

(86) PCT No.: PCT/EP2018/082618
§ 371 (c)(1),
(2) Date: May 21, 2020

(87) PCT Pub. No.: WO2019/102020
PCT Pub. Date: May 31, 2019

(65) Prior Publication Data
US 2020/0355766 A1 Nov. 12, 2020

Related U.S. Application Data

(60) Provisional application No. 62/590,716, filed on Nov. 27, 2017.

(51) Int. Cl.
*G01R 33/36* (2006.01)
*A61B 5/055* (2006.01)
*G01R 33/34* (2006.01)

(52) U.S. Cl.
CPC .......... *G01R 33/3692* (2013.01); *A61B 5/055* (2013.01); *G01R 33/34092* (2013.01); *G01R 33/3628* (2013.01)

(58) Field of Classification Search
CPC ............ G01R 33/3692; G01R 33/3628; G01R 33/34092; A61B 5/055
See application file for complete search history.

(56) References Cited

U.S. PATENT DOCUMENTS 5,666,055 A * 9/1997 Jones ................. G01R 33/3415
324/318
7,176,689 B2 * 2/2007 Machida ............ G01R 33/3415
324/318

(Continued)

OTHER PUBLICATIONS

International Search Report and Written Opinion from PCT/EP2018/082618 dated Mar. 4, 2019.

(Continued)

*Primary Examiner* — Dixomara Vargas

(57) ABSTRACT

A wireless magnetic resonance (MR) signal receiving system comprises a wireless MR coil (20) and a base station (50). The wireless MR coil includes coil elements (22) tuned to receive an MR signal, and electronic modules (24) each including a transceiver (30) and a digital processor (32). Each electronic module is operatively connected to receive an MR signal from at least one coil element. The base station includes a base station transceiver (52) configured to wirelessly communicate with the transceivers of the electronic modules of the wireless MR coil, and a base station digital processor (54). The electronic modules form a configurable mesh network (60) to wirelessly transmit the MR signals received by the electronic modules to the base station. The base station digital processor is programmed to operate the base station transceiver to receive the MR signals wirelessly transmitted to the base station by the configurable mesh network.

22 Claims, 4 Drawing Sheets

(56) References Cited

U.S. PATENT DOCUMENTS

| | | | | |
|---|---|---|---|---|
| 7,486,077 B2 * | 2/2009 | Hergt | .................. | G01R 33/3415 324/318 |
| 7,535,230 B2 * | 5/2009 | Takagi | ............... | G01R 33/3415 324/318 |
| 7,619,415 B2 * | 11/2009 | Nakabayashi | ......... | G16H 30/40 324/318 |
| 7,696,752 B2 * | 4/2010 | Takamori | ............ | G01R 33/3415 324/307 |
| 8,188,743 B2 * | 5/2012 | Sugiura | ............ | G01R 33/56383 324/318 |
| 8,981,777 B2 * | 3/2015 | Biber | ................. | G01R 33/3415 324/318 |
| 9,513,352 B2 * | 12/2016 | Bulumulla | ......... | G01R 33/3692 |
| 9,733,322 B2 * | 8/2017 | Hardie | ............... | G01R 33/3692 |
| 9,817,091 B2 * | 11/2017 | Ishii | ................. | G01R 33/3692 |
| 10,353,024 B2 * | 7/2019 | Tomiha | ............ | G01R 33/34084 |
| 2007/0210793 A1 * | 9/2007 | Kiefer | ................ | G01R 33/3664 324/307 |
| 2008/0129296 A1 * | 6/2008 | Fischer | .............. | G01R 33/3415 324/318 |
| 2008/0143332 A1 * | 6/2008 | Hergt | ................. | G01R 33/3642 324/318 |
| 2008/0197849 A1 * | 8/2008 | Heid | ................ | G01R 33/56375 324/318 |
| 2008/0246477 A1 * | 10/2008 | Nakabayashi | ..... | G01R 33/3692 324/312 |
| 2009/0224761 A1 * | 9/2009 | Umeda | ................ | G01R 33/485 324/312 |
| 2010/0176809 A1 * | 7/2010 | Biber | ................. | G01R 33/3692 324/309 |
| 2011/0031970 A1 * | 2/2011 | Ninomiya | .............. | A61B 5/055 324/309 |
| 2011/0103491 A1 | 5/2011 | Saes et al. | | |
| 2012/0249135 A1 * | 10/2012 | Albsmeier | ......... | G01R 33/3692 324/307 |
| 2012/0306494 A1 * | 12/2012 | Yang | .................. | G01R 33/3664 324/318 |
| 2012/0319689 A1 * | 12/2012 | Ichinose | .......... | G01R 33/56383 324/322 |
| 2013/0200894 A1 | 8/2013 | Albsmeier et al. | | |
| 2013/0241547 A1 | 9/2013 | Biber | | |
| 2014/0091791 A1 * | 4/2014 | Bulumulla | ......... | G01R 33/3642 324/309 |
| 2014/0184222 A1 * | 7/2014 | Seeber | ............... | G01R 33/3875 324/318 |
| 2014/0218034 A1 * | 8/2014 | Ishii | .................. | G01R 33/3692 324/322 |
| 2014/0361769 A1 * | 12/2014 | Hardie | ................... | G01R 33/34 324/307 |
| 2015/0192651 A1 | 7/2015 | Wiehl | | |
| 2016/0109541 A1 | 4/2016 | Hayakawa et al. | | |
| 2016/0154074 A1 * | 6/2016 | Okamoto | ........... | G01R 33/3692 324/322 |
| 2017/0093170 A1 * | 3/2017 | Saunamaki | ............. | H02J 5/005 |
| 2017/0252578 A1 * | 9/2017 | Halkola | ............. | G01R 33/4812 |

OTHER PUBLICATIONS

Elsami et al. "A Survey on Wireless Mesh Networks: Architecture, Specifications and Challenges" 2014 IEEE 5th Control ans System Graduate Research Colloquium, Aug. 11-12, 2014.

* cited by examiner

MESH NETWORKS IN WIRELESS MRI RF COIL

CROSS REFERENCE TO RELATED APPLICATIONS

This application is a U.S. national phase application of International Application No. PCT/EP2018/082618 filed on Nov. 27, 2018, which claims the benefit of U.S. Application Ser. No. 62/590,716 filed on Nov. 27, 2017 and is incorporated herein by reference.

FIELD

The following relates generally to the magnetic resonance (MR) imaging arts, wireless MR receive coil arts, MR signal processing arts, and related arts.

BACKGROUND

Coils consisting of a plurality of coil elements are increasingly common, as such a coil array can provide parallel imaging data acquisition and consequently faster data acquisition and/or higher image resolution and/or higher SNR (signal to noise ratio). An MR receive coil with a plurality of coil elements may employ many channels to acquire in parallel, e.g. one per coil element. In one illustrative example, a coil may include 48 coil elements and 48 MR signal receive channels. The digital data content produced is approximately 20 Mb/s for each channel after acquisition and compression, or 960 Mb/s for the illustrative 48 channel coil.

The large bandwidth payload may be handled by employing separate coaxial cables to carry each channel, but this leads to an unwieldy cable bundle. In a known improvement, a single electronic module may include preamplifiers and time-domain or frequency-domain multiplexing (TDM or FDM) for two coil elements, thereby halving the number of coaxial cables, but the number of cables is still large.

Another difficulty is the potential for electrical coupling of the cabling to the MR magnetic field gradients or other RF coupling. Replacing the coaxial cables with fiber optical connections can reduce this problem, but the large number of connections (galvanic or fiber optical) remains a problem.

A still further difficulty is the need to limit power consumption. MR-compliant products must meet strict thermal emissions requirements so as to not present a burn hazard for patients who might come into contact with the product. Thus, the MR coil should not generate an unacceptable level of heating.

The following discloses certain improvements.

SUMMARY

In some embodiments disclosed herein, a wireless magnetic resonance (MR) coil comprises coil elements tuned to receive an MR signal, and electronic modules each including a transceiver and a digital processor. Each electronic module is operatively connected to receive an MR signal from at least one coil element. The electronic modules form a configurable mesh network to wirelessly transmit the MR signals received by the electronic modules to a base station.

In some embodiments disclosed herein, a wireless MR signal receiving system comprises a wireless MR coil and a base station. The wireless MR coil includes coil elements tuned to receive an MR signal, and electronic modules each including a transceiver and a digital processor. Each electronic module is operatively connected to receive an MR signal from at least one coil element. The base station includes a base station transceiver configured to wirelessly communicate with the transceivers of the electronic modules of the wireless MR coil, and a base station digital processor. The electronic modules form a configurable mesh network to wirelessly transmit the MR signals received by the electronic modules to the base station. The base station digital processor is programmed to operate the base station transceiver to receive the MR signals wirelessly transmitted to the base station by the configurable mesh network.

In some embodiments disclosed herein, a wireless MR signal receiving method comprises: receiving MR signals from coil elements of a wireless MR coil at electronic modules of the wireless MR coil; and operating transceivers of the electronic modules of the wireless MR coil as a configurable mesh network to wirelessly transmit the MR signals received by the electronic modules to a base station.

One advantage resides in a wireless MR coil configurable to provide optimally reduced power consumption.

Another advantage resides in a wireless MR coil configurable to provide optimally reduced heat generation and consequently improved patient safety.

Another advantage resides in a wireless MR coil with improved reliability.

Another advantage resides in a wireless MR coil configurable to provide optimized image quality.

Another advantage resides in a wireless MR coil with improved robustness against failure of one or a few electronic modules of the wireless MR coil.

Another advantage resides in a wireless MR coil configurable to provide dynamic matching of the operational coil elements to the MR imaging field of view (FOV).

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
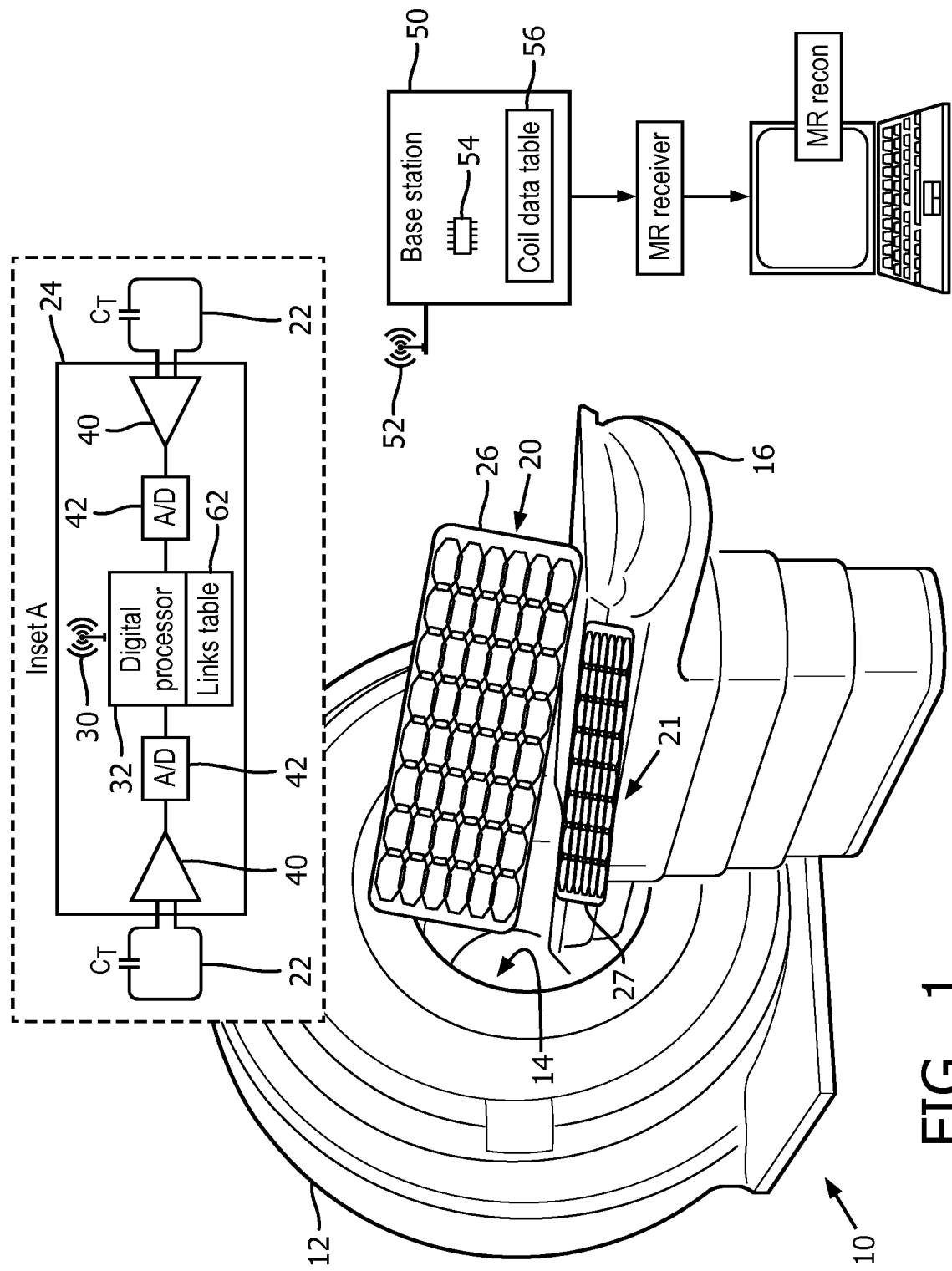
FIG. 1 diagrammatically illustrates a magnetic resonance (MR) imaging device including a wireless MR receive coil and associated RF coil base station.

With reference to FIG. 1, an illustrative medical imaging device 10 comprises a magnetic resonance (MR) imaging scanner, which in the illustrative example includes a housing or gantry 12 containing various components which are not shown in FIG. 1, such as by way of non-limiting illustrative example a superconducting or resistive magnet generating a static ($B_0$) magnetic field, magnetic field gradient coils for superimposing magnetic field gradients on the $B_0$ magnetic field, a whole-body radio frequency (RF) coil for applying RF pulses to excite and/or spatially encode magnetic resonance in an imaging subject disposed in an MR bore 14 or other MR examination region, and/or so forth. A robotic patient couch 16 or other subject support enables loading a medical patient, a subject undergoing a medical screening, or other imaging subject into the MR bore 14 for imaging.

Figure 2:
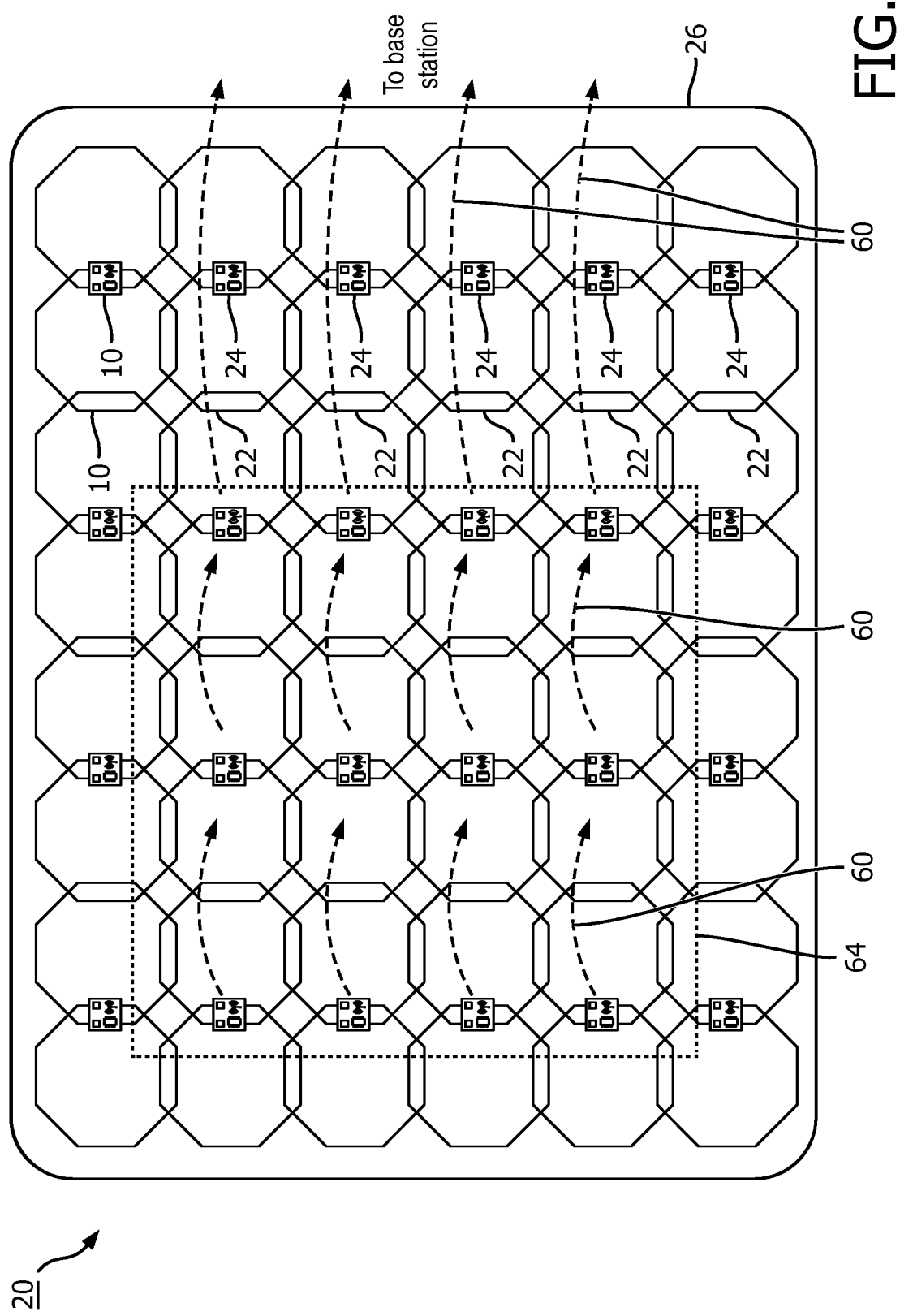
FIG. 2 diagrammatically illustrates a plan view of the wireless MR receive coil of FIG. 1, with an illustrative FOV and communication links between electronic modules of the wireless MR receive coil operating in a suitable mesh configuration indicated.
Figure 3:
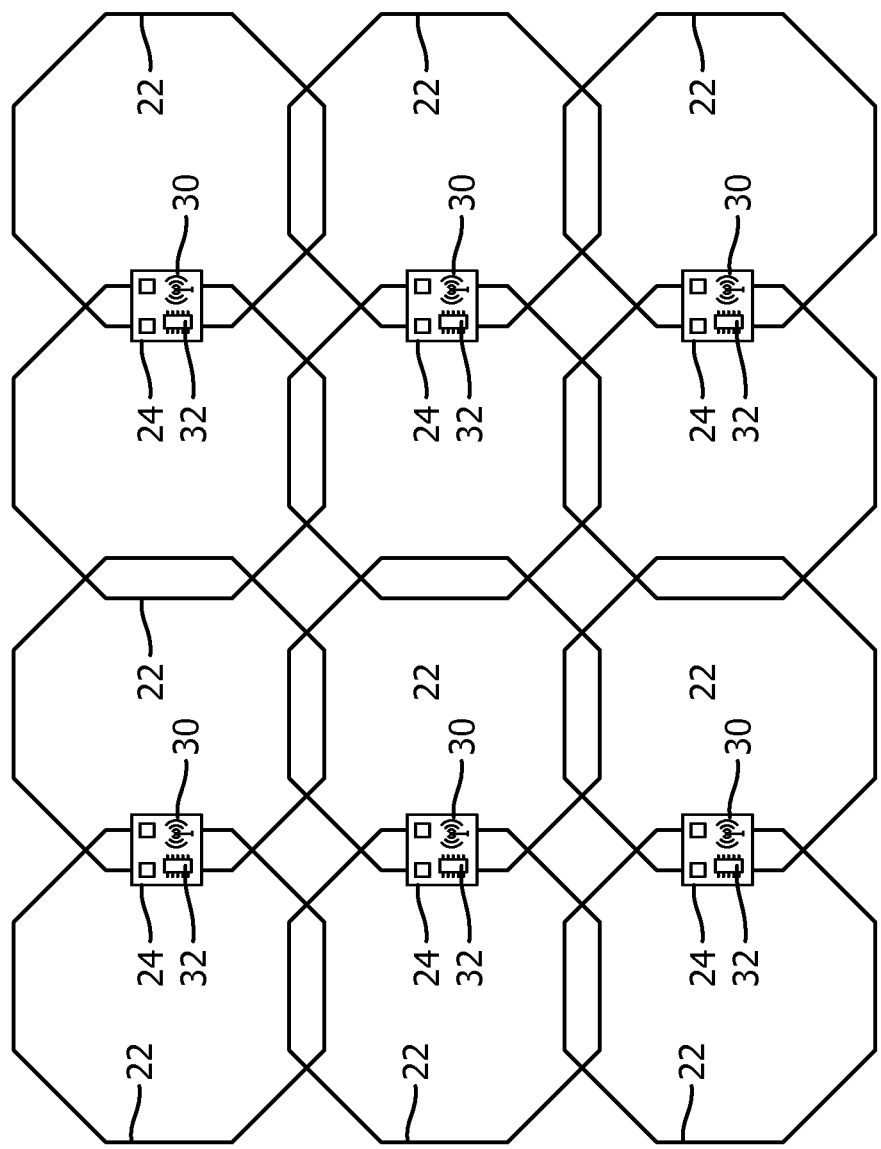
FIG. 3 diagrammatically illustrates an enlarged plan view of one-quarter of the wireless MR receive coil of FIG. 1.

With continuing reference to FIG. 1 and with further reference to FIGS. 2 and 3, a wireless MR coil 20 is provided for receiving the MR signal generated by operation of the MR imaging scanner 10. FIG. 2 shows a plan view of the entire illustrative wireless MR coil 20, while FIG. 3 shows an enlarged view of one-fourth of the illustrative wireless MR coil 20. As best seen in FIGS. 2 and 3, the wireless MR coil 20 includes coil elements 22 tuned to receive an MR signal, and electronic modules 24 operatively connected to receive MR signals from the coil elements 22. The illustrative wireless MR coil 20 includes 48 coil elements 22 arranged in a 6×8 array; however, it will be appreciated that this arrangement is merely an illustrative example and that more or fewer than 48 coil elements may be used in various arrangements, e.g. by way of a few further non-limiting illustrative examples the wireless MR coil may include a one-dimensional arrangement (i.e. linear array) of 4, 8, 12, or more coil elements; or may include a two-dimensional arrangement of N·M coil elements arranged in a regular N×M array (in the illustrative case of wireless MR coil 20, N=6 and M=8 so that N·M=48); or may include a two-dimensional arrangement of coil elements that are not arranged in a regular N×M array. The illustrative 48 coil elements 22 are arranged on a single support or substrate 26; however, as the coil elements disclosed herein are wireless elements it is alternatively contemplated for the coil elements to be arranged on two or more different supports or substrates, e.g. in another contemplated configuration the wireless MR coil includes a frontside sub-coil 20 with a first set of MR coil elements on a first (front) substrate 26 and a backside sub-coil 21 (see FIG. 1) with a second set of MR coil elements on a second (back) substrate 27 so that the front substrate and its supported coil elements can be placed on a front side of the torso of a patient being imaged, and the back substrate 27 and its supported coil elements can be placed on a back side of the torso of the patient being imaged. Again, these are merely illustrative arrangements and it is to be understood that the wireless MR coil with efficient and configurable communication connectivity as disclosed herein can be constructed with a wide range of suitable physical layouts or arrangements. In general the wireless MR coil can be constructed with any suitable form for a chosen type of imaging, e.g. the illustrative wireless MR coil 20 has the shape of a sheet and may, for example, be disposed on, in, or beneath a pallet (not shown) disposed on the subject couch 16 so as to be arranged to perform imaging of the spine, torso, or the like. Alternatively, the wireless MR coil could be shaped to surround a head (i.e., a head coil), to go around a limb (a limb coil), or so forth.

The coil elements 22 are tuned to receive an MR signal generated by precessing isotopes excited by an RF pulse produced by the MR imaging device 10. The MR signal is at or near an MR frequency $f_{MR}$ given by $f_{MR}=1/2\pi\gamma B_0$ where $B_0$ is the static magnetic field generated by the main magnet of the MR imaging device 10, and $\gamma$ is the gyrometric ratio of the isotope generating the MR signal. For example, the $^1$H isotope has $\gamma$=42.58 MHz/T, while the $^{19}$F isotope has $\gamma$=40.05 MHz/T, and so forth. The coils are tuned to the frequency of the MR signal by any suitable technique, e.g. by adjustment of a capacitance C of a tuning capacitor included in a coil loop having inductance L thereby forming the coil loop as a resonant LC loop with resonance frequency $f_{res}=f_{MR}$ where $f_{res}=1/2\pi\sqrt{LC}$. These are merely illustrative examples. The With particular reference to FIGS. 2 and 3 and with further reference to Inset A of FIG. 1, each electronic module 24 includes a transceiver 30 and a digital processor 32, and each electronic module 24 is operatively connected to receive an MR signal from at least one coil element. In the illustrative example, each illustrative electronic module 24 is operatively connected to receive MR signals from two coil elements 22, as best seen in FIGS. 2 and 3 and as diagrammatically shown in FIG. 1 Inset A. A non-limiting illustrative operative connection of the two coil elements 22 with the electronic coil module 24 is shown in FIG. 1 Inset A, and includes a preamplifier 40 that amplifies the analog MR signal and an analog-to-digital (A/D) converter 42 that converts the amplified MR signal to a digital MR signal that is input to the digital processor 32. In general, the number of coil elements operatively coupled with a single electronic module may be one, two (as illustrated), three, four, or more; however, in some embodiments to avoid undue wiring complexity and undesirably long connection lengths from the coils to the preamplifiers, the number of coil elements operatively coupled with a single electronic module is preferably no more than four coil elements. The digital processor 32 may be any suitable programmable digital device or element—for example, the digital processor 32 may be a microprocessor, microcontroller, field programmable gate array (FPGA), or a combination thereof.

The wireless MR coil 20 is a wireless coil that wirelessly transmits the MR signals received by the coil elements 22 off the coil 20 using the transceivers 30 of the electronic modules 24. Furthermore, it is contemplated for the electronic modules 24 to be powered by energy harvesting (e.g., from the RF and/or magnetic fields generated by the MR scanner 10) and/or by on-board rechargeable batteries (not shown) so as to eliminate all wired connections with the system. As such, in some embodiments (including the illustrative embodiment) the wireless MR coil 20 does not include any coaxial cables. In some embodiments (including the illustrative embodiment) the wireless MR coil 20 does not include any optical fibers. In some embodiments (including the illustrative embodiment) the wireless MR coil 20 does not include any coaxial cables and does not include any optical fibers. Alternatively, the wireless MR coil may include a coaxial cable for receiving electrical power, and/or fiber optical connection for delivering a d.c. signal to detune the coil elements 22 during the RF transmit phase of an MR imaging sequence executed by the MR scanner 10, or for some other purpose other than transmitting the MR signals received by the coil elements off the coil. The transceivers 30 of the electronic modules 24 communicate using any suitable low power, short range wireless communication protocol, e.g. ZigBee®, ANT™, WiFi, Bluetooth™, or so forth.

With particular reference to FIGS. 1 and 2, a base station 50 includes a base station transceiver 52 and a base station digital processor 54 (e.g. a microprocessor, microcontroller, FPGA, or a combination thereof, or so forth) which is programmed to operate the base station transceiver 52 to receive the MR signals wirelessly transmitted to the base station 50 by a configurable mesh network (to be described) formed by the electronic modules 24 of the wireless MR coil 20. To facilitate operative communication with the wireless MR coil 20, the base station 50 may include a non-volatile memory (e.g. flash memory) storing a coil data table 56 with information such as the number of MR receive channels (which may in some embodiments correspond to the number of coil elements 22, e.g. 48 channels in the illustrative example), the wireless network IDs of the electronic modules 24 of the wireless MR coil 20 (e.g. hard coded, or obtained by polling the electronic modules 24 in accord with the chosen wireless communication protocol), and may also store information on the physical layout of the coil elements 22 in order to map the coil elements to a particular MR imaging field of view (FOV).

The base station 50 receives the wireless MR signals wirelessly transmitted off the coil 20 using the transceivers 30 of the electronic modules 24. As diagrammatically indicated in FIG. 2, to perform this transmission in an efficient and configurable manner, the electronic modules 24 of the wireless MR coil 20 form a configurable mesh network to wirelessly transmit the MR signals received by the electronic modules 24 to the base station 50. In FIG. 2 dashed arrows indicate pairwise links between electronic modules 24 so as to diagrammatically illustrate the configurable mesh network 60. The configurable mesh network 60 is configurable at least in that each electronic module 24 is programmable to relay an MR signal from at least one different electronic module 24 to at least one other different electronic module 24 or to the base station 50. In diagrammatic FIG. 1 Inset A, the programming of the illustrative electronic module 24 is achieved by way of a links table 62 which stores identification of the other electronic modules for which the illustrative electronic module 24 acts as MR signal relay. In the case of temporary pairings, e.g. using a Bluetooth™ protocol, the pairing key or the like may be stored in the links table 62. The links table 62 may, for example, be stored in a flash memory or other non-volatile memory, or in RAM or other volatile memory. In some embodiments, the wireless communication may employ frequency domain multiplexing (FDM), time domain multiplexing (TDM), orthogonal encoding, or another approach for interleaving transmissions between electronic modules 24 and between electronic modules 24 and the base station 50 in frequency space, time, or by orthogonality of the transmitted signals.

Configuration of the configurable mesh network 60 entails defining which electronic modules serve as relays for which other electronic modules, and which electronic module(s) send MR signal data to the base station 50. The configurable mesh network may be configured to achieve various purpose (s) during an imaging sequence, such as to minimize total power to wirelessly transmit the MR signals received by the electronic modules 24 to the base station 50 (and thereby minimize thermal heating introduced by the wireless MR coil 20 and hence enhance patient comfort and safety); to maximize the minimum signal strength of any wireless communication link of the configurable mesh network (and thereby enhance reliability); and/or so forth. In one approach, the base station 50 serves as a central coordinator for configuring the configurable mesh network 60. To this end, in one illustrative approach the base station digital processor 54 is further programmed to perform mesh configuration operations including: polling the electronic modules 24 of the wireless MR coil 22 using the base station transceiver 52; optimizing a mesh configuration of the configurable mesh network 60 respective to at least one operational metric of the wireless MR coil to generate an optimized mesh configuration (where the operational metric of the wireless MR coil 20 is calculated using information determined from the polling); and transmitting a control signal to control the electronic modules 24 of the wireless MR coil 20 to form the configurable mesh network in accord with the optimized mesh configuration. The operational metric is chosen to enforce the desired optimization. For example, if the desired optimization is to minimize power consumption then the operational metric may be $\Sigma_{i \in \{M\}} P_i$ or $1/|M| \Sigma_{i \in \{M\}} P_i$ or a similar metric, which is to be minimized, where $\{M\}$ is the set of electronic modules 24, $\leq|M|$ is the number of electronic modules 24, and $P_i$ is the power consumption of electronic module indexed by i for a test mesh configuration ($P_i$ may be determined empirically by executing a test communication using the test mesh configuration, or computed based on a polled "per channel" power consumption and the number of module-module or module-base station channel pairings being supported by the module i in the test mesh configuration). As another example, if the desired optimization is to maximize the minimum signal strength of any wireless communication link of the configurable mesh network, then the operational metric may be min $(S_1, S_2, \ldots, S_L)$ or a similar metric, which is to be maximized, where $S_l$ is the signal strength of the module-module or module-base station transmission link indexed l and L denotes the total number of such transmission links in the mesh configuration under test. These are merely examples. See, e.g. Eslami et al., "A Survey on Wireless Mesh Networks: Architecture, Specifications and Challenges", 2014 IEEE 5th Control and System Graduate Research Colloquium, August 11-12, Ui™, Shah Alam, Malaysia, pp. 219-222 (2014) for other mesh configuration examples. The control signal to control the electronic modules 24 of the wireless MR coil 20 to form the configurable mesh network in accord with the optimized mesh configuration may, for example, be a sequence of pair identifiers identifying the module-module and module-base station pairings to be established to implement the optimized mesh configuration.

Another optional aspect of configuration of the configurable mesh network 60 is selection of the operating coil elements. For example, the configurable mesh network 60 may be configurable at least in that the electronic modules 24 are configurable to disable coil elements 22 not coupled to an MR imaging field of view (FOV) 64 (see FIG. 2). In some instances, the MR imaging FOV may be smaller than the area covered by the coil elements 22, so that some coil elements are not (well) coupled with the MR imaging FOV 64. To account for this, the base station digital processor 54 may be further programmed to map the MR imaging FOV (for example, received from the MR imaging device 10 upon the latter being set up to perform a certain imaging sequence) to a set of coil elements of the wireless MR coil 20 and to operate the base station transceiver 52 to transmit a wireless mesh configuration signal to the electronic modules 24 of the wireless MR coil 20 identifying the set of coil elements. The mapped coil elements are those that are (well) coupled with the MR imaging FOV. The configurable mesh network 60 of the wireless MR coil 20 is then configured with respect to the FOV aspect by the electronic modules 24 disabling those of the coil elements 22 that are not included in the set of coil elements identified as coupled to the FOV by the wireless mesh configuration signal.

By way of illustration, the configurable mesh network 60 shown in FIG. 2 is configured in that only the 4×4 array of coil elements within the indicated MR imaging FOV 64 are active (all other coil elements being disabled by the operatively connected electronic modules 24 as part of the mesh configuration). Further, the leftmost four electronic modules 24 of this 4×4 array pair with those four modules next to the right, and so forth, with the rightmost four electronic modules of the 4×4 array pairing with the base station 50 to communicate the MR signals to the base station 50. Such a mesh configuration is efficient in terms of power consumption since the transmission lengths are minimized (thus minimizing the operational metric $\Sigma_{i\in\{M\}} P_i$), and is efficient in terms of reliability as the short transmission lengths are expected to have high signal strengths (thus maximizing the operational metric $\min(S_1, S_2, \ldots, S_L)$). This is merely an illustrative example, and a different mesh configuration may be achieved by optimization for a different operational metric or a different arrangement of the wireless MR receive coil 20 (e.g., if the base station is located "above" the coil in FIG. 2 then the relay links would preferably run from the bottommost electronic modules to the topmost electronic modules which would finally relay to the base station). More generally, the disclosed approach facilitates scalability of the imaging area for applications such as whole body imaging. The disclosed mesh network MR coil design approaches support rapid scalability of imaging area for multi-coil applications, and all the coil elements used in a scan do not need to reside in a single physical MR coil. A mesh network can be made of MR receive elements in multiple MR coils. This is an advantage of the disclosed mesh approach for MR coil design, i.e. the MR receive coil elements can be located in different MR coils across the system, and dynamically combined in a given mesh configuration. This facilitates extension of coil development to non-anatomical coils design, in that one MR coil can support a variety of imaging protocols as long as the coil can receive MR signal sufficient to contribute to the diagnostic image.

Figure 4:
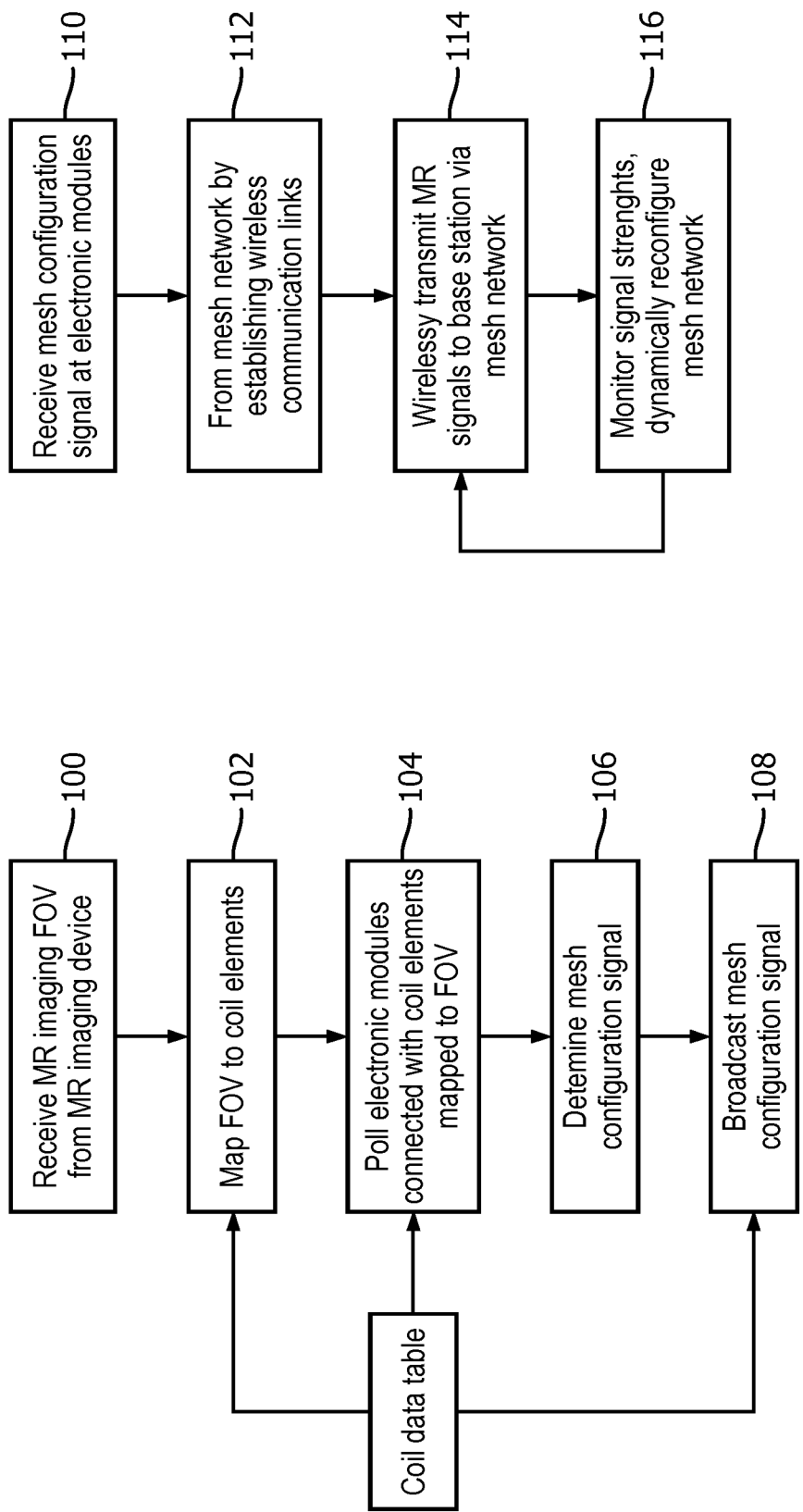
FIG. 4 diagrammatically illustrates a mesh configuration method suitably performed by the wireless MR receive coil and/or the RF coil base station of FIG. 1.

With reference to FIG. 4, an illustrative operation of the wireless MR coil 20 and base station 50 is diagrammed. In an operation 100, the base station 50 receives the MR imaging FOV. In an operation 102 performed by the base station digital processor 54, the MR imaging FOV is mapped to the coil elements that are (well) coupled with the FOV. In an operation 104, the base station digital processor 54 operates the base station transceiver 52 to poll the electronic modules 24 (or, in a variant embodiment, only those modules controlling the coil elements coupled with the MR imaging FOV) to determine information for optimizing the mesh configuration, such as module-module and module-base station pairing signal strengths, per-module power consumption, and/or so forth. In an operation 106, the base station digital processor 54 optimizes the mesh configuration respective to at least one operational metric of the wireless MR coil to generate an optimized mesh configuration. Optionally, this optimization may entail only those electronic modules operatively coupled with coil elements used to image the MR imaging FOV. In an operation 108, the optimized mesh configuration signal (or control signals for implementing the optimized mesh configuration) is broadcast from the base station transceiver 52 to the transceivers 30 of the electronic modules 24. (Alternatively, a current mesh network of the electronic modules may be utilized to relay this information to the modules to perform the operation 108).

In an operation 110, the mesh configuration signal is received at the electronic modules 24 (or at those modules controlling coil elements that are not disabled as not coupled with the FOV), and in an operation 112 the electronic modules 24 form the optimized mesh network by establishing wireless communication links (i.e. module-module links and module-base station links as appropriate to implement the optimized mesh network). In a subsequent ongoing operation 114, the electronic modules wirelessly transmit the received MR signals to the base station 50 using the implemented optimized mesh network.

As the ongoing MR signal offloading operation 114 is continuing, in an optional diagnostic operation 116 the electronic modules 24 and/or the base station 50 may monitor signal strengths, module power consumption, or other operational parameters of the wireless MR coil 20, and if issues are detected (e.g. a link with unacceptably low signal strength, an overheating electronic module, or so forth) the mesh network may be reconfigured to alleviate the detected issue (e.g. by rerouting the mesh network to eliminate the low signal strength link, or by rerouting some mesh network traffic away from the overheating electronic module, or so forth.

In the illustrative example of FIG. 4, the optimized mesh configuration is determined by the base station 50 in operations 102, 106, which is an advantageous approach since the base station 50 may typically have greater data processing capacity, and/or more operational power. However, in other contemplated embodiments the electronic modules 24 may determine or adjust the mesh configuration based on local signal strength measurements, individual module power consumption values, or so forth.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A wireless magnetic resonance (MR) coil, comprising:
   coil elements tuned to receive an MR signal; and
   electronic modules each including a transceiver and a digital processor, wherein each electronic module is operatively connected to receive an MR signal from at least one coil element;
   wherein the electronic modules form a configurable mesh network to wirelessly transmit the MR signals received by the electronic modules to a base station,
   wherein at least one electronic module is configured to be programmable to relay an MR signal from at least one different electronic module in the configurable mesh network to at least one other different electronic module in the configurable mesh network, and
   wherein the at least one electronic module is further configured to be programmable to relay an MR signal from the at least one different electronic module in the configurable mesh network to the base station.

2. The wireless MR coil of claim 1, wherein the configurable mesh network is configurable at least in that the electronic modules are configurable to disable coil elements not coupled to an MR imaging field of view (FOV).

3. The wireless MR coil of claim 1, wherein the configurable mesh network is configurable to minimize total power to wirelessly transmit the MR signals received by the electronic modules to the base station.

4. The wireless MR coil of claim 1, wherein the configurable mesh network is configurable to maximize the minimum signal strength of any wireless communication link of the configurable mesh network.

5. The wireless MR coil of claim 1, wherein the electronic modules form the configurable mesh network in accord with a wireless mesh configuration signal received from the base station.

6. The wireless MR coil of claim 1, wherein the digital processors of the electronic modules comprise microprocessors, microcontrollers, field programmable gate arrays (FPGAs), or a combination thereof.

7. The wireless MR coil of claim 1, wherein each electronic module is operatively connected to receive MR signals from no more than four coil elements.

8. The wireless MR coil of claim 1, wherein each electronic module is configured to be programmable to relay an MR signal from at least one different electronic module in the configurable mesh network to at least one other different electronic module in the configurable mesh network, and wherein each electronic module is further configured to be programmable to relay an MR signal from the at least one different electronic module in the configurable mesh network to the base station.

9. A wireless magnetic resonance (MR) signal receiving system, comprising:
   a wireless MR coil comprising coil elements tuned to receive an MR signal and electronic modules each including a transceiver and a digital processor, wherein each electronic module is operatively connected to receive an MR signal from at least one coil element; and
   a base station comprising a base station transceiver configured to wirelessly communicate with the transceivers of the electronic modules of the wireless MR coil and a base station digital processor;
   wherein the electronic modules form a configurable mesh network to wirelessly transmit the MR signals received by the electronic modules to the base station,
   wherein the base station digital processor is programmed to operate the base station transceiver to receive the MR signals wirelessly transmitted to the base station by the configurable mesh network,
   wherein at least one electronic module is configured to be programmable to relay an MR signal from at least one different electronic module in the configurable mesh network to at least one other different electronic module in the configurable mesh network, and
   wherein the at least one electronic module is further configured to be programmable to relay an MR signal from the at least one different electronic module in the configurable mesh network to the base station.

10. The wireless MR signal receiving system of claim 9, wherein:
    the base station digital processor is further programmed to map an MR imaging field of view (FOV) to a set of coil elements of the wireless MR coil and to operate the base station transceiver to transmit a wireless mesh configuration signal to the electronic modules of the wireless MR coil identifying the set of coil elements;
    wherein the configurable mesh network of the wireless MR coil is configurable at least in that the electronic modules are configurable to disable coil elements not included in the set of coil elements identified by the wireless mesh configuration signal.

11. The wireless MR signal receiving system of claim 9, wherein the base station digital processor is further programmed to perform mesh configuration operations including:
    polling the electronic modules of the wireless MR coil using the base station transceiver;
    optimizing a mesh configuration of the configurable mesh network respective to at least one operational metric of the wireless MR coil to generate an optimized mesh configuration wherein the operational metric of the wireless MR coil is calculated using information determined from the polling; and
    transmitting a control signal to control the electronic modules of the wireless MR coil to form the configurable mesh network in accord with the optimized mesh configuration.

12. The wireless MR signal receiving system of claim 11, wherein the optimizing of the mesh configuration comprises:
    optimizing the mesh configuration to minimize operational power consumed by the wireless MR coil as calculated using power consumption values for the electronic modules determined from the polling.

13. The wireless MR signal receiving system of claim 11, wherein the optimizing of the mesh configuration comprises:
    optimizing the mesh configuration to maximize the minimum signal strength of any wireless communication link of the configurable mesh network as calculated using signal strength values between pairs of electronic modules determined from the polling.

14. The wireless MR signal receiving system of claim 9, wherein the transceivers of the electronic modules and the base station transceiver of the base station wirelessly intercommunicate using time domain multiplexing (TDM) or frequency domain multiplexing (FDM).

15. The wireless MR signal receiving system of claim 9, wherein the wireless MR coil includes a first wireless MR coil with MR coil elements on a first substrate and a second wireless MR coil with MR coil elements on a second substrate.

16. The wireless MR signal receiving system of claim 9, wherein each electronic module is configured to be programmable to relay an MR signal from at least one different electronic module in the configurable mesh network to at least one other different electronic module in the configurable mesh network, and wherein each electronic module is further configured to be programmable to relay an MR signal from the at least one different electronic module in the configurable mesh network to the base station.

17. A wireless magnetic resonance (MR) signal receiving method, comprising:
    receiving a plurality of MR signals from coil elements of a wireless MR coil at electronic modules of the wireless MR coil;
    operating transceivers of the electronic modules of the wireless MR coil as a configurable mesh network to wirelessly transmit the plurality of MR signals received by the electronic modules to a base station,
    wherein wirelessly transmitting the MR signals received by the electronic modules to the base station includes:
        at least a first electronic module in the configurable mesh network relaying an MR signal among the plurality of MR signals from a second electronic module in the configurable mesh network to at least a third electronic module in the configurable mesh network, and
        the third electronic module relaying the MR signal to the base station.

18. The wireless MR signal receiving method of claim 17, further comprising:
    at the base station, mapping an MR imaging field of view (FOV) to a set of coil elements of the wireless MR coil;
    wirelessly transmitting a wireless mesh configuration signal identifying the set of coil elements from the base station to the electronic modules of the wireless MR coil; and by operation of the electronic modules, disabling coil elements not included in the set of coil elements identified by the wireless mesh configuration signal.

19. The wireless MR signal receiving method of claim 17, further comprising:

polling the electronic modules of the wireless MR coil using a base station transceiver of the base station;

at the base station, optimizing a mesh configuration of the configurable mesh network respective to at least one operational metric of the wireless MR coil to generate an optimized mesh configuration wherein the operational metric of the wireless MR coil is calculated using information determined from the polling;

using the base station transceiver, transmitting a control signal to control the electronic modules of the wireless MR coil to form the configurable mesh network in accord with the optimized mesh configuration.

20. The wireless MR signal receiving method of claim 19, wherein the optimizing of the mesh configuration comprises:

optimizing the mesh configuration to minimize operational power consumed by the wireless MR coil as calculated using power consumption values for the electronic modules determined from the polling.

21. The wireless MR signal receiving method of claim 19, wherein the optimizing of the mesh configuration comprises:

optimizing the mesh configuration to maximize the minimum signal strength of any wireless communication link of the configurable mesh network as calculated using signal strength values between pairs of electronic modules determined from the polling.

22. The wireless MR signal receiving method of claim 17, wherein the transceivers of the electronic modules of the wireless MR coil are operated to form the configurable mesh network using time domain multiplexing (TDM) or frequency domain multiplexing (FDM) to wirelessly transmit the MR signals received by the electronic modules to the base station.

* * * * *